United States Patent [19]

Ozato

[11] Patent Number: 5,403,925
[45] Date of Patent: Apr. 4, 1995

[54] NUCLEIC ACIDS ENCODING MAMMALIAN H-2RIIBP OR RXR$_\beta$ AND USES THEREOF

[75] Inventor: Keiko Ozato, Kensington, Md.

[73] Assignee: The United States of America as represented by the Department of Health and Human Services, Washington, D.C.

[21] Appl. No.: 952,800

[22] Filed: Sep. 28, 1992

Related U.S. Application Data

[63] Continuation-in-part of Ser. No. 866,950, Apr. 9, 1992, abandoned, which is a continuation of Ser. No. 450,162, Dec. 13, 1989, abandoned.

[51] Int. Cl.$^6$ .................. C07H 21/02; C07H 21/04; C12Q 1/68
[52] U.S. Cl. ....................... 536/23.5; 435/6; 536/23.1; 536/24.3
[58] Field of Search .................. 435/6; 536/23.1, 23.5

[56] References Cited

PUBLICATIONS

Magnelsdorf, P. et al. Nature 365:224–229 (1990).
Tran, P. et al. MCB 12:4666–4676 (1992).
Hamada et al. (1989) GeneBank deposit printout.
Chambsor et al. (1992) GeneBank Deposit Printout.
Fleischchauer et al. (1992) EMBL deposit printout.
Fleischhauer, K., et al., "Isolation of a Full-Length Clone Encoding a N-Terminally Variant Form of the Human Retinoid X Receptor Beta," *Nuc. Acids Res.* 20:1801 (1992).
Leid, M., et al., "Purification, Cloning, and RXR Identity of the HeLa Cell Factor with Which RAR or TR Heterodimerizes to Bind Target Sequences Efficiently," *Cell* 68:377–395 (1992).
Marks, M. S. et al., et al., "H–2RIIBP (RXRBeta) Heterodimerization Provides a Mechanism for Combinational Diversity in the Regulation of Retinoic Acid and Thyroid Hormone Responsive Genes," *EMBO J.* 11:1419–1435 (1992).
Hamada, K., et al., "H–2RIIBP, a Member of the Nuclear Hormone Receptor Superfamily That Binds to Both the Regulatory Element of Major Histocompatibility Class I Genes and the Estrogen Response Element," *Proc. Natl. Acad. Sci. USA* 86:8289–8293 (1989).
Shirayoshi, Y. et al., "Binding of Multiple Nuclear Factors to the 5' Upstream Regulatory Element of the Murine Major Histocompatibility Class I Gene," *Mol. Cell Biol.* 7:4542–4548 (1987).
Korber, B., et al., "Regulation of Gene Expression by Interferons: Control of H–2 Promoter Responses," *Science* 239:1302–1306 (1988).
Burke, P. A., "Developmental and Tissue–Specific Expression of Nuclear Proteins That Bind the Regulatory Element of the Major Histocompatibiltiy Complex Class I Gene," *J. Exp. Med.* 169:1309–1321 (1989).
Yu, V. C., "RXRBeta: A Coregulator That Enchances Binding of Retionic Acid, Thyroid Hormone, and Vitamin D Receptors to Their Cognate Response Elements," *Cell* 67:1251–1266 (1991).
Marks, M. S., "HR2RIIBP Expressed from a Baculovirus Vector Binds to Multiple Hormone Response Elements," *Mol. Endocrinol.* 6:219:230 (1992).

*Primary Examiner*—Margaret Parr
*Assistant Examiner*—Kenneth R. Horlick
*Attorney, Agent, or Firm*—Townsend and Townsend Khourie and Crew

[57] ABSTRACT

The present invention relates generally to the identification and characterization of new genes and proteins. More particularly, the present invention relates to the discovery of novel members of the nuclear hormone receptor superfamily and cDNA clones thereof. The family members are designated as H-2RIIBP (or RXR$_\beta$, retinoid x receptors). These proteins bind selectively only to the native region II sequence of the conserved major histocompatibility complex class I regulatory element (MHC CRE). Sequences homologous to the H-2RIIBP gene are found in the nuclear receptor family including: retinoic acid receptors (RAR), estrogen receptors (ER), thyroid hormone receptors (TR), (COUP-TF), and other RXR isoformes.

This invention also provides for a diagnostic test which determines the nature and progression of a human tumor by measuring the quantity and quality of H-2RIIBP gene dosage or expression.

3 Claims, No Drawings

NUCLEIC ACIDS ENCODING MAMMALIAN H-2RIIBP OR RXRβ AND USES THEREOF

This application is a continuation-in-part of U.S. Ser. No. 07/866,950, filed Apr. 9, 1992, now abandoned, which was a continuation of U.S. Ser. No. 07/450,162, filed Dec. 13, 1989, and is now abandoned.

The present invention relates generally to the identification and characterization of new genes and proteins. More particularly, the present invention relates to the discovery of novel members of the nuclear hormone receptor superfamily and cDNA clones thereof. The family members are retinoid receptors and are designated H-2 region II binding proteins [H-2RIIBP].

BACKGROUND OF THE INVENTION

MHC class I genes encode transplantation antigens that play important roles in immune responses. Transcription of major histocompatibility complex (MHC) class I genes is regulated by the conserved MHC class I regulatory element (CRE). In the MHC CRE there are at least three sequences, regions I, II and III that bind nuclear factors. Region I binding activity is expressed only in tissues that express MHC class I genes at high levels, while the region II factor is detected in various tissues irrespective of the MHC class I gene expression. While proteins that bind to various regions of the MHC CRE are known, a protein that binds selectively only to the native region II sequence, but not to the other sequences of the MHC CRE, has not heretofore been known or described. This family of receptors is the subject of the present invention.

More particularly, these nuclear hormone receptors belong to the steroid/thyroid hormone receptor superfamily of transcriptional regulators. The compositions of this invention are retinoid X receptors (RXRs). They are highly conserved proteins and the sequences provided herein are useful for identification and isolation of homologous genes in all mammals.

SUMMARY OF THE INVENTION

This invention provides for an isolated DNA sequence encoding a mammalian H-2RIIBP, said DNA encoding H-2RIIBP having at least 95% amino acid identity with the amino acid sequence of Seq. ID No. 1. A preferred mammalian H-2RIIBP is the human H-2RIIBP and Seq. ID No. 1 provides an example of a human H-2RIIBP.

In addition to the above DNA sequences, this invention provides substantially pure and isolated mammalian H-2RIIBP having at least 95% amino acid identity with the amino acid sequence of Seq. ID No. 1. The murine H-2RIIBP is an example of such a protein species. The preferred mammalian H-2RIIBP is the human H-2RIIBP.

This invention also provides for antibodies specifically immunoreactive with the mammalian H-2RIIBP identified above.

The proteins of this invention are useful in methods for determining the status of a human tumor, the progression of which is dependent on the tissue level of human H-2RIIBP, said method comprising: measuring the amount of H-2RIIBP in the tumor tissue specimen by determining the quantity of H-2RIIBP specific biologics, said biologics being selected from the group consisting of: (a) mRNA encoding H-2RIIBP; (b) DNA encoding H-2RIIBP; and, (c) H-2RIIBP; wherein the H-2RIIBP has 95% amino acid identity with Seq. ID. No. 1.

The proteins of this invention are also useful in the method described above wherein the quantitative measurement of the amount of H-2RIIBP is by an immunoassay comprising: (a) contacting the tumor tissue with an antibody specific to H-2RIIBP under conditions permitting the binding between the antibody and H-2RIIBP; and, (b) detecting the level of binding between said antibody and tissue; wherein the H-2RIIBP has 95% amino acid identity with Seq. ID. No. 1.

Furthermore this invention provides a method as described above wherein the quantitative measurement of the amount of H-2RIIBP is by a nucleic acid hybridization assay comprising (a) contacting of the tumor tissue with a nucleic acid probe specific for binding to H-2RIIBP encoding nucleic acid under conditions permitting binding between the probe and the H-2RIIBP nucleic acid and (b) detecting the level of binding between said the probe and H-2RIIBP encoding nucleic acid.

Finally, this invention provides for diagnostic kits comprising a container containing a biologic able to selectively bind to a target entity wherein the target entity is a mammalian H-2RIIBP or a DNA encoding a mammalian H-2RIIBP. The biologic can be an antibody or a nucleic acid. The H-2RIIBP is as described above.

DEFINITIONS

"Antibody" refers to an immunoglobulin molecule able to bind to a specific epitope on an antigen. Antibodies can be a polyclonal mixture or monoclonal. Antibodies can be intact immunoglobulins derived from natural sources or from recombinant sources and can be immunoreactive portions of intact immunoglobulins. Affinity constants of $1 \times 10^8$ liters/mole are preferred. Antibodies are typically tetramers of immunoglobulin molecules. The antibodies may exist in a variety of forms including, for example, Fv, Fab, and F(ab)$_2$, as well as in single chains (e.g., Huston, et al., *Proc. Nat. Acad. Sci. U.S.A.*, 85:5879–5883 (1988) and Bird, et al., *Science* 242:423–426 (1988), which are incorporated herein by reference). (See generally, Hood, et al., "Immunology", Benjamin, N.Y., 2nd ed. (1984), and Hunkapiller and Hood, *Nature*, 323:15–16 (1986), which are incorporated herein by reference). Single-chain antibodies, in which genes for a heavy chain and a light chain are combined into a single coding sequence, may also be used.

"Biologic" refers to compositions derived from biological sources. Antibodies and nucleic acids are examples of such materials.

"Complementary" means that one nucleic acid is identical to, or hybridizes selectively to, another nucleic acid. Selectivity of hybridization exists when hybridization occurs that is more selective than total lack of specificity. Typically, selective hybridization will occur when there is at least about 55% identity over a stretch of at least 14–25 nucleotides, preferably at least about 65%, more preferably at least about 75%, and most preferably at least about 90%. See, M. Kanehisa *Nucleic Acids Res.* 12:203 (1984), incorporated herein by reference.

"H-2RIIBP" refers to a family of retinoid receptors having at least 95% amino acid identity with the sequence of ID No. 1. It is understood that H-2RIIBP includes those naturally occurring proteins which make up the family of mammalian H-2RIIBP including polymorphic forms in the same mammalian species. But the term further includes nonnatural mutations introduced by deliberate mutation using conventional recombinant technology such as single site mutation or by excising short sections of DNA encoding H-2RIIBP or by substituting new amino acids or adding new amino acids. Such minor alterations must substantially maintain the immunoidentity of the original molecule and/or its biological properties. Particular modifications considered minor would include substitution of amino acids of similar chemical properties, e.g., glutamic acid for aspartic acid or glutamine for asparagine. By aligning a protein optimally with the protein of Seq. ID No. 2 and by using the conventional immunoassays described herein, one can readily determine proteins described by this invention.

"Isolated" or "substantially pure", when referring to nucleic acids, refers to those that have been purified away from other chromosomal or extrachromosomal DNA or RNA by standard techniques, including alkaline/SDS treatment, CsCl banding, column chromatography, and other techniques well known in the art. See, F. Ausubel, et al., ed. *Current Protocols in Molecular Biology*, Greene Publishing and Wiley-Interscience, New York (1987), incorporated herein by reference.

"Isolated DNA sequence" refers to deoxyribonucleic acid sequences which are cDNA when derived from reverse transcription of a messenger RNA.

"95% amino acid identity" refers to a comparison of the amino acids of two polypeptides which when optimally aligned have approximately 95% of the same amino acids.

"Nucleic acids", as used herein, may be DNA or RNA. Additionally, substantial nucleic acid sequence identity exists when a nucleic acid segment will hybridize, under stringent hybridization conditions, to a complement of another nucleic acid strand.

"Nucleic acid probes" may be DNA fragments prepared, for example, by digesting plasmid DNA, or by PCR as discussed above, or synthesized by either the phosphoramidite method described by Beaucage and Carruthers, *Tetrahedron Lett.* 22:1859–1862 (1981), or by the triester method according to Matteucci, et al., *J. Am. Chem. Soc.*, 103:3185 (1981), both incorporated herein by reference. A double stranded fragment may then be obtained, if desired, by annealing the chemically synthesized single strands together under appropriate conditions or by synthesizing the complementary strand using DNA polymerase with an appropriate primer sequence. Where a specific nucleic acid sequence is given, it is understood that the complementary strand is also identified and included. For the complementary strand will work equally well in situations where the target is a double-stranded nucleic acid.

A nucleic acid probe is complementary to a target nucleic acid when it will anneal only to a single desired position on that target nucleic acid under conditions determined as described below. Proper annealing conditions depend, for example, upon a probe's length, base composition, and the number of mismatches and their position on the probe, and must often be determined empirically.

For discussions of nucleic acid probe design and annealing conditions, see, for example, Sambrook et al., *Molecular Cloning: A Laboratory Manual* (2nd ed.), Vols. 1–3, Cold Spring Harbor Laboratory, (1989) or *Current Protocols in Molecular Biology*, F. Ausubel et al., ed. Greene Publishing and Wiley-Interscience, New York (1987), both of which are incorporated herein by reference.

"Nucleic acid sequence" refers to a single- or double-stranded polymer of deoxyribonucleotide or ribonucleotide bases read from the 5' to the 3' end. It includes both self-replicating plasmids, infectious polymers of DNA or RNA and nonfunctional DNA or RNA.

"Specifically immunoreactive" refers to a binding reaction between an antibody and antigen which is determinative of the presence of the antigen in the presence of a heterogeneous population of proteins and other biologics.

"Substantially pure" as used herein means that the protein is as pure as can be obtained by standard isolation and purification means. Typically this means at least 80% pure as determined by SDS polyacrylamide gel electrophoresis.

DETAILED DESCRIPTION

The compositions of this invention relate to nuclear hormone receptors for use in diagnosing the progression of cancerous cells in a host, monitoring abnormal metabolism of thyroid hormone, retinoid and vitamin D.

Biologically, these proteins are intracellular receptors which mediate the effects of steroid and thyroid hormones as well as the metabolites of vitamin A (retinoic acid). Upon hormone binding, some receptors are translocated from the cytoplasm to the nucleus where they control the transcriptional expression of certain hormone-responsive genes. This involves the binding of the receptors—often in homo- or heterodimeric form—to specific sequences in the target gene promoter.

The members of this genus of proteins have a characteristic tripartite modular structure consisting of (1) a highly conserved central region containing the $C_4/C_5$ zinc-finger domain which is responsible for binding to DNA; (2) a relatively well-conserved C-terminal part which contains the hormone binding sites and mediates dimerization with other hormone receptors; and (3) a variable N-terminal domain which has been implicated in transactivation or repression of target genes.

The proteins of this invention also bind to major histocompatibility complex (MHC) class I genes in response to retinoic acid. In humans, the H-2RIIBP gene is located on chromosome 6.

The murine H-2RIIBP, also designated RXR$\beta$, was initially identified because of its ability to bind to the regulatory region II in the murine major histocompatibility complex (MHC) class I promoter. Therefore the family of proteins is also referred to as H-2 region II binding protein or H-2RIIBP (Hamada et al., 1989). The RXR subfamily consists of at least three similar genes, RXR$\alpha$, RXR$\beta$ and RXR$\gamma$, all of which control transcription of target genes mediated by retinoids (Mangelsdorf et al., 1992). An isomer of retinoic acid, 9-cis retinoic acid, has recently been shown to specifically bind to RXRs, thus activating transcription of a RXR response element.

H-2RIIBP controls expression of many genes that respond to hormones and vitamins, including thyroid hormone, retinoids, Vitamin A and Vitamin D (in addition to estrogen). H-2RIIBP controls expression of the unusually large arrays of genes because it has the unusual ability to heterodimerize with other hormone receptors, namely the thyroid hormone receptors, Vitamin D receptor, and retinoic acid receptors (Marks, S. M., Hallenbeck, P. L., Nagata, T., Segars, H. J., Appella, E., Nikodem, V., and Ozato, K., EMBO. J. 11:1419-1435, 1992).

H-2RIIBP is suspected to be the cause of some disease conditions involving defects in metabolizing retinoids, thyroid hormone, and vitamin D, since H-2RIIBP controls gene expression mediated by these agents. H-2RIIBP is also believed to dictate responsiveness by some cancers (skin, lung and other cancers) to certain types of therapeutic treatment (particularly steroid and retinoids).

Furthermore, H-2RIIBPs are shown to have a strong tendency to heterodimerize with several other nuclear hormone receptors, controlling expression of a large set of target genes.

H-2RIIBP RNA and its DNA and mRNA appear in many cells and tissues of the human body. By following the method herein one can evaluate the quality and quantity of H-2RIIBP expressed in cells/tissues. The expression of H-2RIIBP could signify the nature of certain cancer cells, and could indicate the cause of certain metabolic defects seen in disease conditions involving steroid/thyroid, and some vitamins.

The quantity and quality of H-2RIIBP serve as diagnostic criteria. Because H-2RIIBP interferes with the estrogen action, estrogen dependent cancers such as breast cancers and ovarian cancers are a good target for diagnostic use. In addition, determining the expression of H-2RIIBP would help diagnose some types of skin cancers, leukemia, lung cancers and cervical cancers, and would help identify a course of treatment for such cancers. Determining the expression of H-2RIIBP would also facilitate the determination of the cause of some metabolic abnormalities such as thyroid hyper- or hypo-sensitivity, resistance to vitamin D and vitamin A/retinoid treatment. Endocrine abnormalities such as estrogen resistance are also included. The levels of H-2RIIBP may be measured by RNA hybridization and by various immunological means for cancerous and metabolically pathological cells and tissues.

The determination of the levels and quality of H-2RIIBP can be achieved by using nucleic acid probes specific for H-2RIIBP. By using a DNA fragment containing the H-2RIIBP nucleic acid sequence cloned in plasmids, one can determine the levels of H-2RIIBP, this would involve nucleic acid (RNA) hybridization of nucleic acids prepared from cancerous (or diseased) tissues with a H-2RIIBP probe in a stringent condition. The quality and quantity can be determined by radioimmunoassay, ELISA, immunohistochemical assay, and SDS PAGE assay by using antibodies specific for H-2RIIBP. A PCR based detection may also be used for quick identification of H-2RIIBP. These procedures can be performed on a routine basis in a hospital laboratory with standard equipment. The nucleic acid sequence (a variety of cDNA fragments, genomic DNA) is in the form of the plasmids that grow in bacteria in large quantity, and can be immediately available for use.

Although a conserved product, the H-2RIIBP genes can appear in the human population in different allelic forms. By following the methods disclosed herein, one can evaluate polymorphisms.

More specifically, this invention relates to an isolated nucleic acid sequence encoding mammalian H-2RIIBP and the gene product, H-2RIIBP. The nucleic acid compositions of this invention, whether RNA, cDNA, genomic DNA, or a hybrid of the various combinations, may be isolated from natural sources or may be synthesized in vitro. The preferred natural source is a HeLa cell line. The nucleic acids claimed may be present in transformed or transfected whole cells, in a transformed or transfected cell lysate, or in a partially purified or substantially pure form.

Techniques for nucleic acid manipulation of genes encoding H-2RIIBP, such as subcloning nucleic acid sequences encoding polypeptides into expression vectors, labelling probes, DNA hybridization, and the like are described generally, for example in Sambrook et al. (1989) op. cit., or Ausubel et al., ed. (1987) op. cit., both of which are incorporated herein by reference.

Nucleic acid probes for isolating mammalian genes encoding H-2RIIBP are also included in the claimed invention. Such probes are useful for detecting the presence of H-2RIIBP in physiological samples and as primers for gene amplification using polymerase chain reaction [PCR]. The nucleic acid probes will usually be at least about 20 nucleotides in length, more typically they will be more than 500 nucleotides in length.

A method of isolating H-2RIIBP genes is also described herein. Briefly, the nucleic acid sequences can be isolated by probing a DNA library which is comprised of either genomic DNA or cDNA. Libraries may be either from commercial sources or prepared from mammalian tissue by techniques known to those skilled in the art. The preferred cDNA libraries are human cDNA libraries which are available from commercial sources.

The DNA libraries can be probed by plaque hybridization using nucleic acid probes of at least 20 base pairs which are complementary to unique sequences of the human or murine H-2RIIBP genes. The preferred probes are: bases 1 to 250 or 550 to 1300 of Seq. I.D. No. 1 and bases 1 to 250 and 550 to 1300 of Seq. I.D. No. 3.

The nucleic acid probes may be labeled to facilitate isolation of the hybridized clones. Labeling can be by any of the techniques known to those skilled in the art, but typically the probes are labeled with $^{32}P$ using terminal deoxynucleotidyl-transferase.

Alternatively, those of skill may use polymerase chain reaction technology (PCR) to amplify nucleic acid sequences of the H-2RIIBP gene directly from mRNA, from cDNA, from genomic libraries or cDNA libraries. Polymerase chain reaction (PCR) or other in vitro amplification methods may also be useful, for example, to clone nucleic acid sequences that code for proteins to be expressed, to make nucleic acids to use as probes for detecting the presence of H-2RIIBP or H-2RIIBP mRNA in physiological samples, for nucleic acid sequencing, or for other purposes.

Appropriate primers and probes for identifying H-2RIIBP from alternative mammalian tissues are generated from comparisons of the sequences provided herein. For a general overview of PCR see *PCR Protocols: A Guide to Methods and Applications*. (Innis, M, Gelfand, D., Sninsky, J. and White, T., eds.), Academic Press, San Diego (1990), incorporated herein by reference.

In summary, the H-2RIIBP gene can prepared by probing or amplifying select regions of a mixed cDNA or genomic pool using the probes and primers generated from the sequences provided herein.

Once the H-2RIIBP gene is isolated and cloned, one may express the H-2RIIBP gene in a recombinantly engineered cell such as bacteria, yeast, filamentous fungal, insect (especially employing baculoviral vectors), and mammalian cells. It is expected that those of skill in the art are knowledgeable in the numerous expression systems available for expression of the H-2RIIBP gene. No attempt to describe in detail the various methods known for the expression of proteins in prokaryotes or eukaryotes will be made.

In brief summary, the expression of natural or synthetic nucleic acids encoding mammalian H-2RIIBP will typically be achieved by operably linking the gene or cDNA to a promoter (which is either constitutive or inducible), and incorporating into an expression vector. The vectors are suitable for replication and integration in either prokaryotes or eukaryotes. Typical cloning vectors contain transcription and translation terminators, initiation sequences, and promoters useful for regulation of the expression of the H-2RIIBP gene. The vectors may also comprise generic expression cassettes containing at least one independent terminator sequence, sequences permitting replication of the plasmid in both eukaryotes and prokaryotes, i.e., shuttle vectors, and selection markers for both prokaryotic and eukaryotic systems.

Methods for the expression of cloned genes in bacteria are also well known. In general to obtain high level expression of a cloned gene in a prokaryotic system, it is essential to construct expression vectors which contain, at a minimum, a strong promoter to direct mRNA transcription termination. The inclusion of selection markers in DNA vectors transformed in E. coli is also useful. Examples of such markers include genes specifying resistance to ampicillin, tetracycline, or chloramphenicol. See Sambrook for details concerning selection markers and promoters for use in E. coli.

Suitable eukaryote hosts may include plant cells, insect cells, mammalian cells, yeast, and filamentous fungi. In a preferred embodiment of this invention, the baculovirus/insect cell system is used for gene expression.

The protein encoded by the H-2RIIBP gene which is produced by recombinant DNA technology may be purified by standard techniques well known to those of skill in the art. Recombinantly produced H-2RIIBP can be directly expressed or expressed as a fusion protein. The protein is then purified by a combination of cell lysis (e.g., sonication) and affinity chromatography. For fusion products, subsequent digestion of the fusion protein with an appropriate proteolytic enzyme releases the desired H-2RIIBP.

The purified H-2RIIBP when described as "isolated" or and "substantially pure" describes a protein that has been separated from components which naturally accompany it. Typically, a monomeric protein is substantially pure when at least about 85% or more of a sample exhibits a single polypeptide backbone. Minor variants or chemical modifications may typically share the same polypeptide sequence. Depending on the purification procedure, purities of 85%, and preferably over 95% pure are possible. Protein purity or homogeneity may be indicated by a number of means well known in the art, such as polyacrylamide gel electrophoresis of a protein sample, followed by visualizing a single polypeptide band on a polyacrylamide gel upon staining. For certain purposes high resolution will be needed and HPLC or a similar means for purification utilized.

The proteins of this invention may be purified to substantial purity by standard techniques well known in the art, including selective precipitation with such substances as ammonium sulfate, column chromatography, immunopurification methods, and others. See, for instance, R. Scopes, *Protein Purification: Principles and Practice*, Springer-Verlag: New York (1982), incorporated herein by reference.

The present invention also provides methods for detecting the presence or absence and certain types of abnormality of H-2RIIBP in a physiological specimen. One method for evaluating the presence or absence of H-2RIIBP in a sample involves a Southern transfer and is well known to those of skill in the art. Briefly, the digested genomic DNA is run on agarose slab gels in buffer and transferred to membranes. Hybridization is carried out using the probes discussed above. Visualization of the hybridized portions allows the qualitative determination of the presence or absence of H-2RIIBP genes.

Similarly, a Northern transfer may be used for the detection of H-2RIIBP message in samples of RNA. This procedure is also well known in the art. See, Maniatis, et al., *Molecular Cloning: A laboratory manual*, Cold Spring Harbor Laboratory, Cold Spring Harbor, N.Y. (1982). In brief, the mRNA is isolated from a given cell sample using an acid guanidinium-phenol-chloroform extraction method. The mRNA is then electrophoresed to separate the mRNA species and the mRNA is transferred from the gel to a nitrocellulose membrane. As with the Southern blots, labeled probes are used to identify the presence or absence of the H-2RIIBP transcript.

An alternative means for determining the level of expression of the H-2RIIBP gene is in situ hybridization. In situ hybridization assays are well known and are generally described in Angerer, et al., *Methods Enzymol.*, 152:649–660 (1987). In an in situ hybridization cells are fixed to a solid support, typically a glass slide. If DNA is to be probed, the cells are denatured with heat or alkali. The cells are then contacted with a hybridization solution at a moderate temperature to permit annealing of H-2RIIBP specific probes that are labelled. The probes are preferably labelled with radioisotopes or fluorescent reporters.

In addition to the detection of H-2RIIBP genes using nucleic acid hybridization technology, one can use immunoassays to detect the H-2RIIBP product. Immunoassays can be used to qualititatively and quantitatively analyze H-2RIIBP. A general overview of the applicable technology can be found in Harlow and Lane, *Antibodies: A Laboratory Manual*, Cold Spring Harbor Pubs., N.Y. (1988). In brief, H-2RIIBP or a fragment thereof is expressed in transfected cells, preferably bacterial cells, and purified as generally described above and in the examples. The product is then injected into a mammal capable of producing antibodies. Either monoclonal or polyclonal antibodies specific for the gene product can be used in various immunoassays. Such assays include ELISA, competitive immunoassays, radioimmunoassays, western blots, indirect immunofluorescent assays and the like.

Monoclonal antibodies may be obtained by various techniques familiar to those skilled in the art. Briefly, spleen cells from an animal immunized with a desired antigen are immortalized, commonly by fusion with a myeloma cell (see, Kohler and Milstein, *Eur. J. Immunol.* 6:511–519 (1976), incorporated herein by reference). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host.

ELISA is a preferred immunoassay for detecting H-2RIIBP. In brief, tumor tissues obtained from biopsy and stored by quick freezing are homogenized and cytosolic and whole cell extracts are prepared by standard procedures. ELISA plates are coated with recombinant H-2RIIBP in phosphate buffer (pH~7.4). Tissue homogenates are added to the coated ELISA plates and incubated with anti-H-2RIIBP antibody for sufficient time to allow antigen-antibody reaction to take place. Following incubation, a developing antibody is added and the antigen-antibody reaction is quantitatively measured by spectrophotometric or other suitable means. Of course, a normal tissue sample is included in a parallel control run. Such assays determine the level of the H-2RIIBP in the tissues rapidly and accurately. A large part of the procedure may be automated.

Since H-2RIIBP binds to the estrogen response genes, the progression of those tumors which depend on estrogen for their growth, such as certain breast tumors, can now be monitored by periodic determination of the level of H-2RIIBP in suspected cases by the method described herein above. Similarly, therapeutic efficacy of a treatment regimen designed to control the level of H-2RIIBP can be determined by monitoring the level of H-2RIIBP in the treated individual at various times during the course of treatment.

This invention further embraces diagnostic kits for detecting the presence of H-2RIIBP in tissue samples comprises a container containing anti-H-2RIIBP antibodies and instructional material for performing the test.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed or contemplated herein are standard methodologies well known to one of ordinary skill in the art. The materials, methods and examples are illustrative only and not limiting.

EXAMPLES

A. Isolation of cDNA encoding human H-2RIIBP.

The human gene encoding H-2RIIBP was identified by nucleic acid screening of a cDNA library constructed from the human BURKITT lymphoma line DAUDI. A 561 base pair fragment of the murine RXRβ gene (H-2RIIBP) as described in Hamada, K., et al. (1989) *Proc. Natl. Acad. Sci. USA* 86, 8289–8293 and encompassing the zinc-finger coding region was used as a probe. Several positive clones, each 2.9 Kb in size, were identified. One of the these clones, designated DAUDI.6, was shown to contain a large open reading frame that was preceded by two in-frame stop codons. Sequence analysis of this open reading frame predicted a 533 amino acid protein.

A fragment of the hRXRβ1 gene (residues 40 to 458) was PCR-amplified from the cDNA template and hybridized to oligonucleotide probes corresponding to the regions of sequence disparity (including the 16 base pair insertion). Under stringent washing conditions, this method can be used to detect single base mismatches, hRXRβ1 and hRXRβ2 may represent isomers of the human RXRβ which differ only in their N-terminal sequences and have arisen from alternative splicing and/or differential promotor usage. The existence of such isomers has previously been shown for RARα (Leroy, et al. (1991) *EMBO J.* 10, 59-69) β (Zelent et al. (1991) *EMBO J.* 10, 71-81) and τ (Kastner et al. (1990) *Proc. Natl. Acad. Sci. USA* 87, 2700-2704).

B. The expression of H-2RIIBP cDNA in a recombinant baculovirus.

With noted exceptions, the procedure described below was as described by Summers and Smith (1987), *A Manual of Methods for the Baculovirus Vectors for Insect Culture Procedure*, Texas Agricultural Experimental Station Bulletin 1555. In brief, an EcoRI-EcoRI fragment encompassing the entire translatable sequence (446 amino acids) and part of the 3'-untranslated region of human H-2RIIBP was cloned into the transfer plasmid pAc 436. Insect Sf9 cells were cultured at 27° C. in Grace's medium (Gibco, Grand Island, N.Y.) supplemented with 10% fetal bovine serum, 0.33% Yeastolate, 0.33% lactalbumin hydrolysate (Difco, Detroit, Mich.), and antibiotics. Two hours before transfection, the medium was replaced with Dulbecco's Modified Eagle's Medium containing 10% fetal bovine serum. Cells were cotransfected with 0.5 μg baculovirus AcMNPV DNA and 1 μg transfer plasmid by using the standard calcium phosphate precipitation method for 2 h at 32° C. After transfection, cells were maintained in the Grace-based medium as above. Sf9 cells harboring the rH-2RIIBP virus were screened by the method of Pen et al. in *Nucleic Acids Res.* 17:451.

To obtain rH-2RIIBP, Sf9 cells ($10^9$) were infected with the rH-2RIIBP virus (MO $>$1) for 3 days of 27° C. Nuclear and cytoplasmic extracts were prepared according to the method of Dignam et al. (*Nucleic Acids Res* 11:1475–1489) with the following modifications. All buffers contained the proteinase inhibitors phenylmethylsulfonylfluoride (0.5 mM), N-α-p-tosyl-L-lysine chloromethyl ketone (0.1 mM), N-tosyl-L-phenylalanine chloromethyl ketone (0.1 mM), pepstatin-A (10 μg/ml), leupeptin (10 μg/ml), aprotinin (33 μg/ml), and either E-64 (10 μg/ml) or bestatin [10 μg/ml; Sigma (St. Louis, Mo.) or Boehringer Mannheim (Indianapolis, Ind.)]. Materials extracted from nuclei were used without dialysis. Cytoplasmic fractions were prepared by removing nuclei and debris from lysates by centrifugation over a bed of 1.7M sucrose. The yield was 200 to 250 mg/gm of cell.

C. Monoclonal Anti-H-2RIIBP Antibodies

BALB/c female mice were immunized with 20–25 μg nuclear extract proteins prepared from cells infected with the rH-2RIIBP virus in complete Freund's adjuvant. Mice were immunized 3 and 5 weeks later with the same amount of extract, with and without incomplete adjuvant. Three days after a fourth injection in PBS, spleen cells from immune mice were fused with P3X63 cells using 30% polyethylene glycol. Hybridoma cells were selected by hypoxanthine, aminopterin, and thymidine in Dulbecco's Modified Eagle's Medium containing supplement. Hybridomas producing anti-H-2RIIBP antibody were screened by differential enzyme-linked immunosorbent assay. Briefly, culture supernatants (50 μl/well) were placed in a 96 Immunol. I well coated with nuclear extracts from cells infected with the rH-2RIIBP virus or the wild-type virus (5 μg protein/ml). Bound antibodies were detected by peroxidase-coupled goat antimouse immunoglobulin G (IgG; Cappel, Cochranville, Pa.), using tetramethylbenzidine (Miles Scientific, Elkhart, Ind.) as a substrate. Those hybridomas that reacted only with the rH-2RIIBP extracts were scored positive.

Alternatively one can use the peptide representing amino acid positions 184–204 of H-2RIIBP. The peptide is designated H-2RII-1 and provides KREAV-QEERQRGKDKDGDGDGC. The Cystine residue is not naturally occurring and was an artifact of the synthesis procedure. H-2RII-1 was synthesized on an Applied Biosystems 430A synthesizer (Foster City, Calif.). This peptide was coupled with KLH (Calbiochem, La Jolla, Calif.) using m-maleimido-benzoyl-N-hydroxysuccinimide ester. Rabbits were immunized with 100 μg antigen in complete Freund's adjuvant three times through a subcutaneous injection. KLH and the H-2RII-1 peptide were coupled to cyanogen bromide-activated Bio-Gel A50 (Bio-Rad, Richmond, Calif.) or to epoxy-activated Sepharose 6B (Pharmacia, Piscataway, N.J.), respectively. Anti-KLH and anti-H-2RII-1 antibodies were purified by affinity chromatography on columns prepared from these beads and eluted in 3.5M MgCl$_2$ in PBS, followed by extensive dialysis against PBS. To eliminate reactivity to KLH, purified anti-H-2RII-1 antibody was applied to the KLH column, and flow-through fractions were used for experiments. Similarly, control anti-KLH antibody was passed through the H-2RII-1 column before experiments.

D. SDS-PAGE and Western Blot Assays

The following procedure can be used to detect H-2RIIBP in breast tumor tissue. SDS-PAGE is performed according to Laemmli, U. K. (1970) *Nature* 227:680–685 using 10 μg extract protein from the tissue in a 10.5% acrylamide separating gel, and gels are stained with Coomassie brilliant blue R-250. Western blot assays are performed according to Towbin et al. *Proc. Natl. Acad. Sci. USA* 76:4350–4354 with 0.5 μg extract protein, and gels were electrotransferred to reinforced nitrocellulose filters (Schleicher and Schuell, Keene, N.H.). Blots are blocked with Blotto according to Johnson et al. (1984), *Gene Anal. Technol.* 1:3–8 and incubated overnight with undiluted hybridoma supernatant or 10 μg/ml affinity-purified anti-H-2RIIBP peptide antibody (from example C) in Blotto containing 2% normal goat serum. Blots were then washed six times in Blotto, followed by a 2 hour incubation with $^{125}$I-labelled antimouse or antirabbit Ig (Amersham, Arlington Heights, Ill.). Blots were washed six times with Blotto and autoradiographed.

It is understood that the examples and embodiments described herein are for illustrative purposes only and that various modifications or changes in light thereof will be suggested to persons skilled in the art and are to be included within the spirit and preview of this application and scope of the appended claims.

What is claimed is:

1. An isolated DNA sequence encoding a human H-2RIIBP said DNA sequence encoding an H-2RIIBP having the amino acid sequence of Seq. ID No. 2.

2. An isolated DNA sequence having nucleotide sequence of claim 1 provided in Seq. ID No. 1.

3. A diagnostic kit for detecting human H-2RIIBP comprising a container containing a nucleic acid probe of at least 20 nucleotides, said probe selected from the sequence of SEQ ID NO: 1.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 2130 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( C ) INDIVIDUAL ISOLATE: DAUDI
        ( G ) CELL TYPE: T cell lymphoma
        ( H ) CELL LINE: DAUDI ( v i i ) IMMEDIATE SOURCE:
        ( A ) LIBRARY: cDNA DAUDI
        ( B ) CLONE: DAUDI6

( i x ) FEATURE:
        ( A ) NAME/KEY: CDS
        ( B ) LOCATION: 180..1778

( i x ) FEATURE:
        ( A ) NAME/KEY: polyAsignal
        ( B ) LOCATION: 2109..2121

( x i ) SEQUENCE DESCRIPTION: SEQ ID NO:1:

```
GAATTCCGGC  TGCCACATTG  GCGCTGTCAT  TTTGGTACTG  AGCAGAGCGA  CGGGCTTAAT         60

TCGACCCAAT  CCAGGCCAGA  GTCTTTCTCT  CAGGGGCTTC  CTCGTGCTCA  GCTAATCCTC        120

CGATCAATCC  TTGGGAATCC  CTGGGACCTC  TTCGGTATCC  CTACTCTCAG  CCAGGGATC        179

ATG  TCT  TGG  GCC  GCT  CGC  CCG  CCC  TTC  CTC  CCT  CAG  CGG  CAT  GCC  GCA      227
Met  Ser  Trp  Ala  Ala  Arg  Pro  Pro  Phe  Leu  Pro  Gln  Arg  His  Ala  Ala
 1             5                        10                        15
```

```
GGG CAG TGT GGG CCG GTG GGG GTG CGA AAA GAA ATG CAT TGT GGG GTC      275
Gly Gln Cys Gly Pro Val Gly Val Arg Lys Glu Met His Cys Gly Val
         20                      25                  30

GCG TCC CGG TGG CGG CGG CGA CGG CCC TGG CTG GAT CCC GCA GCG GCG      323
Ala Ser Arg Trp Arg Arg Arg Arg Pro Trp Leu Asp Pro Ala Ala Ala
        35                  40                      45

GCG GCG GCG GCG GTG GCA GGC GGA GAA CAA CAA ACC CCG GAG CCG GAG      371
Ala Ala Ala Ala Val Ala Gly Gly Glu Gln Gln Thr Pro Glu Pro Glu
50                      55                      60

CCA GGG GAG GCT GGA CGG GAC GGG ATG GGC GAC AGC GGG CGG GAC TCC     419
 Pro Gly Glu Ala Gly Arg Asp Gly Met Gly Asp Ser Gly Arg Asp Ser
 65                      70                      75              80

CGA AGC CCA GAC AGC TCC TCC CCA AAT CCC CTT CCC CAG GGA GTC CCT      467
Arg Ser Pro Asp Ser Ser Ser Pro Asn Pro Leu Pro Gln Gly Val Pro
                    85                      90                  95

CCC CCT TCT CCT CCT GGG CCA CCC CTA CCC CCT TCA ACA GCT CCA TCC      515
Pro Pro Ser Pro Pro Gly Pro Pro Leu Pro Pro Ser Thr Ala Pro Ser
            100                     105                 110

CTT GGA GGC TCT GGG GCC CCA CCC CCA CCC CCG ATG CCA CCA CCC CCA      563
Leu Gly Gly Ser Gly Ala Pro Pro Pro Pro Pro Met Pro Pro Pro Pro
            115                     120                 125

CTG GGC TCT CCC TTT CCA GTC ATC AGT TCT TCC ATG GGG TCC CCT GGT      611
Leu Gly Ser Pro Phe Pro Val Ile Ser Ser Ser Met Gly Ser Pro Gly
    130                     135                     140

CTG CCC CCT CCA GCT CCC CCA GGA TTC TCC GGG CCT GTC AGC AGC CCC      659
Leu Pro Pro Pro Ala Pro Pro Gly Phe Ser Gly Pro Val Ser Ser Pro
145                     150                     155                 160

CAG ATT AAC TCA ACA GTG TCA CTC CCT GGG GGT GGG TCT GGC CCC CCT      707
Gln Ile Asn Ser Thr Val Ser Leu Pro Gly Gly Gly Ser Gly Pro Pro
                165                     170                 175

GAA GAT GTG AAG CCA CCA GTC TTA GGG GTC CGG GGC CTG CAC TGT CCA      755
Glu Asp Val Lys Pro Pro Val Leu Gly Val Arg Gly Leu His Cys Pro
            180                     185                 190

CCC CCT CCA GGT GGC CCT GGG GCT GGC AAA CGG CTA TGT GCA ATC TGC      803
Pro Pro Pro Gly Gly Pro Gly Ala Gly Lys Arg Leu Cys Ala Ile Cys
            195                     200                 205

GGG GAC AGA AGC TCA GGC AAA CAC TAC GGG GTT TAC AGC TGT GAG GGT      851
Gly Asp Arg Ser Ser Gly Lys His Tyr Gly Val Tyr Ser Cys Glu Gly
210                     215                     220

TGC AAG GGC TTC TTC AAA CGC ACC ATC CGC AAA GAC CTT ACA TAC TCT      899
Cys Lys Gly Phe Phe Lys Arg Thr Ile Arg Lys Asp Leu Thr Tyr Ser
225                     230                     235                 240

TGC CGG GAC AAC AAA GAC TGC ACA GTG GAC AAG CGC CAG CGG AAC CGC      947
Cys Arg Asp Asn Lys Asp Cys Thr Val Asp Lys Arg Gln Arg Asn Arg
                245                     250                 255

TGT CAG TAC TGC CGC TAT CAG AAG TGC CTG GCC ACT GGC ATG AAG AGG      995
Cys Gln Tyr Cys Arg Tyr Gln Lys Cys Leu Ala Thr Gly Met Lys Arg
            260                     265                 270

GAG GCG GTA CAG GAG GAG CGT CAG CGG GGA AAG GAC AAG GAT GGG GAT    1043
 Glu Ala Val Gln Glu Glu Arg Gln Arg Gly Lys Asp Lys Asp Gly Asp
             275                     280                 285

GGG GAG GGG GCT GGG GGA GCC CCC GAG GAG ATG CCT GTG GAC AGG ATC     1091
Gly Glu Gly Ala Gly Gly Ala Pro Glu Glu Met Pro Val Asp Arg Ile
    290                     295                     300

CTG GAG GCA GAG CTT GCT GTG GAA CAG AAG AGT GAC CAG GGC GTT GAG     1139
Leu Glu Ala Glu Leu Ala Val Glu Gln Lys Ser Asp Gln Gly Val Glu
305                     310                     315                 320

GGT CCT GGG GGA ACC GGG GGT AGC GGC AGC AGC CCA AAT GAC CCT GTG     1187
Gly Pro Gly Gly Thr Gly Gly Ser Gly Ser Ser Pro Asn Asp Pro Val
                325                     330                 335

ACT AAC ATC TGT CAG GCA GCT GAC AAA CAG CTA TTC ACG CTT GTT GAG     1235
```

-continued

| | | | | | | | | | | | | | | |
|---|---|---|---|---|---|---|---|---|---|---|---|---|---|---|
|Thr|Asn|Ile|Cys 340|Gln|Ala|Ala|Asp|Lys 345|Gln|Leu|Phe|Thr|Leu 350|Val|Glu|

```
TGG GCG AAG AGG ATC CCA CAC TTT TCC TCC TTG CCT CTG GAT GAT CAG       1283
Trp Ala Lys Arg Ile Pro His Phe Ser Ser Leu Pro Leu Asp Asp Gln
        355                 360             365

GTC ATA TTG CTG CGG GCA GGC TGG AAT GAA CTC CTC ATT GCC TCC TTT       1331
Val Ile Leu Leu Arg Ala Gly Trp Asn Glu Leu Leu Ile Ala Ser Phe
    370                 375                 380

TCA CAC CGA TCC ATT GAT GTT CGA GAT GGC ATC CTC CTT GCC ACA GGT       1379
Ser His Arg Ser Ile Asp Val Arg Asp Gly Ile Leu Leu Ala Thr Gly
385                 390                 395                 400

CTT CAC GTG CAC CGC AAC TCA GCC CAT TCA GCA GGA GTA GGA GCC ATC       1427
Leu His Val His Arg Asn Ser Ala His Ser Ala Gly Val Gly Ala Ile
                405                 410                 415

TTT GAT CGG GTG CTG ACA GAG CTA GTG TCC AAA ATG CGT GAC ATG AGG       1475
Phe Asp Arg Val Leu Thr Glu Leu Val Ser Lys Met Arg Asp Met Arg
            420                 425                 430

ATG GAC AAG ACA GAG CTT GGC TGC CTG AGG GCA ATC ATT CTG TTT AAT       1523
Met Asp Lys Thr Glu Leu Gly Cys Leu Arg Ala Ile Ile Leu Phe Asn
        435                 440                 445

CCA GAT GCC AAG GGC CTC TCC AAC CCT AGT GAG GTG GAG GTC CTG CGG       1571
Pro Asp Ala Lys Gly Leu Ser Asn Pro Ser Glu Val Glu Val Leu Arg
    450                 455                 460

GAG AAA GTG TAT GCA TCA CTG GAG ACC TAC TGC AAA CAG AAG TAC CCT       1619
Glu Lys Val Tyr Ala Ser Leu Glu Thr Tyr Cys Lys Gln Lys Tyr Pro
465                 470                 475                 480

GAG CAG CAG GGA CGG TTT GCC AAG CTG CTG CTA CGT CTT CCT GCC CTC       1667
Glu Gln Gln Gly Arg Phe Ala Lys Leu Leu Arg Leu Pro Ala Leu
                485                 490                 495

CGG TCC ATT GGC CTT AAG TGT CTA GAG CAT CTG TTT TTC TTC AAG CTC       1715
Arg Ser Ile Gly Leu Lys Cys Leu Glu His Leu Phe Phe Phe Lys Leu
            500                 505                 510

ATT GGT GAC ACC CCC ATC GAC ACC TTC CTC ATG GAG ATG CTT GAG GCT       1763
Ile Gly Asp Thr Pro Ile Asp Thr Phe Leu Met Glu Met Leu Glu Ala
        515                 520                 525

CCC CAT CAA CTG GCC TGAGCTCAGA CCCAGACGTG GTGCTTCTCA CACTGGAGGA       1818
Pro His Gln Leu Ala
    530

GCACACATCC AAGAGGGACT CCAAGCCCTG GGGAGGGTGG GGGGCCATGT TCCCAGAACC    1878

TTGATGGGGT GAGAAGTACA GGGCAGAACC AAGAACATAA ACCCTCCAAG GGATCTGCTT    1938

GATATCCCAA GTTGGAAGGG ACCCCAGATA CCTGTGAGGA CTGGTTGTCT CTCTTCGGTG    1998

CCCTTGAGTC TCTGAATTTG CATGATTTTT GCCCTGCGTC CCTTCTCTTT GGGGCTCCTT    2058

TCCCCTCTCA TACATAAAAT CGCTTTCAAA TTAAAATCGC TGTTTCTGG AAAAAAAAA     2118

AAAGGCCTTA AG                                                       2130
```

( 2 ) INFORMATION FOR SEQ ID NO:2:

( i ) SEQUENCE CHARACTERISTICS:
        ( A ) LENGTH: 533 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Ser Trp Ala Ala Arg Pro Pro Phe Leu Pro Gln Arg His Ala Ala
 1               5                   10                  15

Gly Gln Cys Gly Pro Val Gly Val Arg Lys Glu Met His Cys Gly Val
            20                  25                  30

Ala Ser Arg Trp Arg Arg Arg Arg Pro Trp Leu Asp Pro Ala Ala Ala
```

-continued

|   |   |   |   | 35 |   |   |   |   | 40 |   |   |   |   | 45 |   |   |
|---|---|---|---|---|---|---|---|---|---|---|---|---|---|---|---|---|

Ala Ala Ala Ala Val Ala Gly Gly Glu Gln Gln Thr Pro Glu Pro Glu
                  50              55              60

Pro Gly Glu Ala Gly Arg Asp Gly Met Gly Asp Ser Gly Arg Asp Ser
65              70              75              80

Arg Ser Pro Asp Ser Ser Pro Asn Pro Leu Pro Gln Gly Val Pro
                  85              90              95

Pro Pro Ser Pro Pro Gly Pro Pro Leu Pro Pro Ser Thr Ala Pro Ser
            100             105             110

Leu Gly Gly Ser Gly Ala Pro Pro Pro Pro Met Pro Pro Pro Pro
        115             120             125

Leu Gly Ser Pro Phe Pro Val Ile Ser Ser Ser Met Gly Ser Pro Gly
        130             135             140

Leu Pro Pro Pro Ala Pro Pro Gly Phe Ser Gly Pro Val Ser Ser Pro
145             150             155             160

Gln Ile Asn Ser Thr Val Ser Leu Pro Gly Gly Ser Gly Pro Pro
                  165             170             175

Glu Asp Val Lys Pro Pro Val Leu Gly Val Arg Gly Leu His Cys Pro
            180             185             190

Pro Pro Pro Gly Gly Pro Gly Ala Gly Lys Arg Leu Cys Ala Ile Cys
        195             200             205

Gly Asp Arg Ser Ser Gly Lys His Tyr Gly Val Tyr Ser Cys Glu Gly
    210             215             220

Cys Lys Gly Phe Phe Lys Arg Thr Ile Arg Lys Asp Leu Thr Tyr Ser
225             230             235             240

Cys Arg Asp Asn Lys Asp Cys Thr Val Asp Lys Arg Gln Arg Asn Arg
                  245             250             255

Cys Gln Tyr Cys Arg Tyr Gln Lys Cys Leu Ala Thr Gly Met Lys Arg
            260             265             270

Glu Ala Val Gln Glu Glu Arg Gln Arg Gly Lys Asp Lys Asp Gly Asp
        275             280             285

Gly Glu Gly Ala Gly Gly Ala Pro Glu Glu Met Pro Val Asp Arg Ile
    290             295             300

Leu Glu Ala Glu Leu Ala Val Glu Gln Lys Ser Asp Gln Gly Val Glu
305             310             315             320

Gly Pro Gly Gly Thr Gly Gly Ser Gly Ser Ser Pro Asn Asp Pro Val
                  325             330             335

Thr Asn Ile Cys Gln Ala Ala Asp Lys Gln Leu Phe Thr Leu Val Glu
            340             345             350

Trp Ala Lys Arg Ile Pro His Phe Ser Ser Leu Pro Leu Asp Asp Gln
        355             360             365

Val Ile Leu Leu Arg Ala Gly Trp Asn Glu Leu Leu Ile Ala Ser Phe
    370             375             380

Ser His Arg Ser Ile Asp Val Arg Asp Gly Ile Leu Leu Ala Thr Gly
385             390             395             400

Leu His Val His Arg Asn Ser Ala His Ser Ala Gly Val Gly Ala Ile
                  405             410             415

Phe Asp Arg Val Leu Thr Glu Leu Val Ser Lys Met Arg Asp Met Arg
            420             425             430

Met Asp Lys Thr Glu Leu Gly Cys Leu Arg Ala Ile Ile Leu Phe Asn
        435             440             445

Pro Asp Ala Lys Gly Leu Ser Asn Pro Ser Glu Val Glu Val Leu Arg
    450             455             460

Glu Lys Val Tyr Ala Ser Leu Glu Thr Tyr Cys Lys Gln Lys Tyr Pro
465             470             475             480

```
Glu Gln Gln Gly Arg Phe Ala Lys Leu Leu Leu Arg Leu Pro Ala Leu
                485             490             495

Arg Ser Ile Gly Leu Lys Cys Leu Glu His Leu Phe Phe Lys Leu
        500             505             510

Ile Gly Asp Thr Pro Ile Asp Thr Phe Leu Met Glu Met Leu Glu Ala
        515             520             525

Pro His Gln Leu Ala
530
```

(2) INFORMATION FOR SEQ ID NO:3:

(i) SEQUENCE CHARACTERISTICS:
    (A) LENGTH: 2204 base pairs
    (B) TYPE: nucleic acid
    (C) STRANDEDNESS: single
    (D) TOPOLOGY: linear (ii) MOLECULE TYPE: cDNA (ix) FEATURE:
    (A) NAME/KEY: CDS
    (B) LOCATION: 1..1338

(xi) SEQUENCE DESCRIPTION: SEQ ID NO:3:

```
GAA TTC CCC CGA AGC CCA GAC AGC TCC TCC CCA AAT CCC CTT TCT CAG     48
Glu Phe Pro Arg Ser Pro Asp Ser Ser Ser Pro Asn Pro Leu Ser Gln
 1               5                  10                  15

GGG ATC CGT CCG TCT TCT CCT CCT GGC CCA CCT CTT ACC CCT TCA GCA     96
Gly Ile Arg Pro Ser Ser Pro Pro Gly Pro Pro Leu Thr Pro Ser Ala
                20                  25                  30

CCT CCA CCT CCA ATG CCA CCC CCG CCA CTG GGC TCC CCC TTC CCA GTC    144
Pro Pro Pro Pro Met Pro Pro Pro Pro Leu Gly Ser Pro Phe Pro Val
            35                  40                  45

ATC AGT TCT TCC ATG GGG TCC CCT GGT CTG CCC CCT CCG GCT CCC CCA    192
Ile Ser Ser Ser Met Gly Ser Pro Gly Leu Pro Pro Pro Ala Pro Pro
        50                  55                  60

GGA TTC TCC GGG CCT GTC AGC AGC CCT CAG ATC AAC TCC ACA GTG TCG    240
Gly Phe Ser Gly Pro Val Ser Ser Pro Gln Ile Asn Ser Thr Val Ser
 65                  70                  75                  80

CTC CCT GGG GGT GGG TCT GGC CCC CCT GAA GAT GTG AAG CCA CCG GTC    288
Leu Pro Gly Gly Gly Ser Gly Pro Pro Glu Asp Val Lys Pro Pro Val
                85                  90                  95

TTA GGG GTC CGG GGC CTG CAC TGT CCA CCC CCT CCA GGT GGT CCT GGG    336
Leu Gly Val Arg Gly Leu His Cys Pro Pro Pro Pro Gly Gly Pro Gly
                100                 105                 110

GCT GGC AAA CGG CTC TGT GCA ATC TGC GGG GAC CGA AGC TCA GGC AAG    384
Ala Gly Lys Arg Leu Cys Ala Ile Cys Gly Asp Arg Ser Ser Gly Lys
            115                 120                 125

CAC TAT GGG GTT TAC AGC TGC GAG GGC TGC AAG GGT TTC TTC AAG CGC    432
His Tyr Gly Val Tyr Ser Cys Glu Gly Cys Lys Gly Phe Phe Lys Arg
        130                 135                 140

ACC ATT CGG AAG GAC CTG ACC TAC TCG TGT CGT GAT AAC AAA GAC TGT    480
Thr Ile Arg Lys Asp Leu Thr Tyr Ser Cys Arg Asp Asn Lys Asp Cys
145                 150                 155                 160

ACA GTG GAC AAG CGC CAG CGG AAT CGC TGT CAG TAC TGT CGC TAT CAG    528
Thr Val Asp Lys Arg Gln Arg Asn Arg Cys Gln Tyr Cys Arg Tyr Gln
                165                 170                 175

AAG TGC CTG GCC ACT GGC ATG AAA AGG GAG GCG GTT CAG GAG GAG CGT    576
Lys Cys Leu Ala Thr Gly Met Lys Arg Glu Ala Val Gln Glu Glu Arg
            180                 185                 190

CAA CGG GGG AAG GAC AAA GAC GGG GAT GGA GAT GGG GCT GGG GGA GCC    624
Gln Arg Gly Lys Asp Lys Asp Gly Asp Gly Asp Gly Ala Gly Gly Ala
        195                 200                 205
```

| | | | | | | | | | | | | | | | | |
|---|---|---|---|---|---|---|---|---|---|---|---|---|---|---|---|---|
| CCT | GAG | GAG | ATG | CCT | GTG | GAC | AGG | ATC | CTG | GAG | GCA | GAG | CTT | GCT | GTG | 672 |
| Pro | Glu | Glu | Met | Pro | Val | Asp | Arg | Ile | Leu | Glu | Ala | Glu | Leu | Ala | Val | |
| | 210 | | | | 215 | | | | | 220 | | | | | | |
| GAG | CAG | AAG | AGT | GAC | CAA | GGC | GTT | GAG | GGT | CCT | GGG | GCC | ACC | GGG | GGT | 720 |
| Glu | Gln | Lys | Ser | Asp | Gln | Gly | Val | Glu | Gly | Pro | Gly | Ala | Thr | Gly | Gly | |
| 225 | | | | | 230 | | | | | 235 | | | | | 240 | |
| GGT | GGC | AGC | AGC | CCA | AAT | GAC | CCA | GTG | ACT | AAC | ATC | TGC | CAG | GCA | GCT | 768 |
| Gly | Gly | Ser | Ser | Pro | Asn | Asp | Pro | Val | Thr | Asn | Ile | Cys | Gln | Ala | Ala | |
| | | | | 245 | | | | | 250 | | | | | 255 | | |
| GAC | AAA | CAG | CTG | TTC | ACA | CTC | GTT | GAG | TGG | GCA | AAG | AGG | ATC | CCG | CAC | 816 |
| Asp | Lys | Gln | Leu | Phe | Thr | Leu | Val | Glu | Trp | Ala | Lys | Arg | Ile | Pro | His | |
| | | | 260 | | | | | 265 | | | | | 270 | | | |
| TTC | TCC | TCC | CTA | CCT | CTG | GAC | GAT | CAG | GTC | ATA | CTG | CTG | CGG | GCA | GGC | 864 |
| Phe | Ser | Ser | Leu | Pro | Leu | Asp | Asp | Gln | Val | Ile | Leu | Leu | Arg | Ala | Gly | |
| | | 275 | | | | | 280 | | | | | 285 | | | | |
| TGG | AAC | GAG | CTC | CTC | ATT | GCG | TCC | TTC | TCC | CAT | CGG | TCC | ATT | GAT | GTC | 912 |
| Trp | Asn | Glu | Leu | Leu | Ile | Ala | Ser | Phe | Ser | His | Arg | Ser | Ile | Asp | Val | |
| | 290 | | | | | 295 | | | | | 300 | | | | | |
| CGA | GAT | GGC | ATC | CTC | CTG | GCC | ACG | GGT | CTT | CAT | GTG | CAC | AGA | AAC | TCA | 960 |
| Arg | Asp | Gly | Ile | Leu | Leu | Ala | Thr | Gly | Leu | His | Val | His | Arg | Asn | Ser | |
| 305 | | | | | 310 | | | | | 315 | | | | | 320 | |
| GCC | CAT | TCC | GCA | GGC | GTG | GGA | GCC | ATC | TTT | GAT | CGG | GTG | CTG | ACA | GAG | 1008 |
| Ala | His | Ser | Ala | Gly | Val | Gly | Ala | Ile | Phe | Asp | Arg | Val | Leu | Thr | Glu | |
| | | | | 325 | | | | | 330 | | | | | 335 | | |
| CTA | GTG | TCC | AAA | ATG | CGT | GAC | ATG | AGG | ATG | GAC | AAG | ACA | GAG | CTT | GGC | 1056 |
| Leu | Val | Ser | Lys | Met | Arg | Asp | Met | Arg | Met | Asp | Lys | Thr | Glu | Leu | Gly | |
| | | | 340 | | | | | 345 | | | | | 350 | | | |
| TGC | CTG | CGG | GCA | ATC | ATA | CTG | TTT | AAT | CCA | GAC | GCC | AAG | GGC | CTC | TCC | 1104 |
| Cys | Leu | Arg | Ala | Ile | Ile | Leu | Phe | Asn | Pro | Asp | Ala | Lys | Gly | Leu | Ser | |
| | | 355 | | | | | 360 | | | | | 365 | | | | |
| AAC | CCT | GGA | GAG | GTG | GAG | ATC | CTT | CGG | GAG | AAG | GTG | TAC | GCC | TCA | CTG | 1152 |
| Asn | Pro | Gly | Glu | Val | Glu | Ile | Leu | Arg | Glu | Lys | Val | Tyr | Ala | Ser | Leu | |
| | 370 | | | | | 375 | | | | | 380 | | | | | |
| GAG | ACC | TAT | TGC | AAG | CAG | AAG | TAC | CCT | GAG | CAG | CAG | GGC | CGG | TTT | GCC | 1200 |
| Glu | Thr | Tyr | Cys | Lys | Gln | Lys | Tyr | Pro | Glu | Gln | Gln | Gly | Arg | Phe | Ala | |
| 385 | | | | | 390 | | | | | 395 | | | | | 400 | |
| AAG | CTG | CTG | TTA | CGT | CTT | CCT | GCC | CTC | CGC | TCC | ATC | GGC | CTC | AAG | TGT | 1248 |
| Lys | Leu | Leu | Leu | Arg | Leu | Pro | Ala | Leu | Arg | Ser | Ile | Gly | Leu | Lys | Cys | |
| | | | | 405 | | | | | 410 | | | | | 415 | | |
| CTG | GAG | CAC | CTG | TTC | TTC | TTC | AAG | CTC | ATT | GGC | GAC | ACC | CCC | ATT | GAC | 1296 |
| Leu | Glu | His | Leu | Phe | Phe | Phe | Lys | Leu | Ile | Gly | Asp | Thr | Pro | Ile | Asp | |
| | | | 420 | | | | | 425 | | | | | 430 | | | |
| ACC | TTC | CTC | ATG | GAG | ATG | CTT | GAG | GCT | CCC | CAC | CAG | CTA | GCC | | | 1338 |
| Thr | Phe | Leu | Met | Glu | Met | Leu | Glu | Ala | Pro | His | Gln | Leu | Ala | | | |
| | | 435 | | | | | 440 | | | | | 445 | | | | |

| | | | | | |
|---|---|---|---|---|---|
| TGAGCCCAGA | TGCACACCGA | GTGTCACTGA | GGAGGACTTG | AGCCTGGGCA | GGGGGCAGAG | 1398 |
| CCATGGGACA | GGTGCAGAGC | AGGAGGGGAC | TTGCCCAGCC | TGCCAGGGAT | CTGGCAACAC | 1458 |
| TTAGCAGGGT | TCGCTTGGTC | TCCAAGTCGA | AGGGGACCCC | AGATCCCTGT | GAGGACTTTA | 1518 |
| TGTCTACCTT | CAGTGGCCTT | GAGTCTCTGA | ATTTGTCGGG | GTCTCCCATG | GTGCAGGTGA | 1578 |
| TTCTTCATCC | TGGCTCCCCA | GCACAAAGCA | CTGCCCTGCT | TCCTTCTCAT | TTGGCCTCAC | 1638 |
| TCCCTTCTGA | AGAGTGGAAC | AGAGCTCCCC | CAGAAAGGGG | TGTTGTGGGG | CAGGCCCCCC | 1698 |
| AAGCTGATGA | TCATGGGAGC | AGGGCTCTGA | CAGCCTTTAT | CCTCTCAGAC | TTGACAGATG | 1758 |
| GGGCAGAGG | AGGGACCTGC | CTCTGTCTCC | TGTCAGCCCC | ATTTCCACAG | TCCCTCCTGC | 1818 |
| AGTCAGACTG | AAGAATAAAG | GGGTAGTGAA | GGGGCTGCTG | GAGGTGGAGG | AACCCATTGC | 1878 |
| TCTTTTAATT | TCCTGTGAGG | AGAGACTGGG | AGTTAGACTC | AAAGAAGTAC | TGTACATCCC | 1938 |
| CAGGTTGACT | TAAATGTCAG | GGCTGGAGAT | GGCATGTGGG | CAAGGAGGCC | CCTCAGGTGG | 1998 |

-continued

```
GCTGTCCCAA AGCTCCCTGG GCTCTGCCTC GGGTGGCCCT ACAGCTCTTC CCTAGTCTTA    2058

AGCACAGCTA GGCTGGGAGC AAGTGGGGAC ATTGATGGGG GTGGCCAGCC TGCAGAGTTG    2118

GGTGCTGGGC TGCATGGTTT TTGCCCTGGA CCTCTTTTGG GGGTTCCCTC CCATCTTTCA    2178

CTTGCACATA AAGTTGCTTT CCAGTT                                        2204
```

( 2 ) INFORMATION FOR SEQ ID NO:4:

( i ) SEQUENCE CHARACTERISTICS:
( A ) LENGTH: 446 amino acids
( B ) TYPE: amino acid
( D ) TOPOLOGY: linear ( i i ) MOLECULE TYPE: protein ( x i ) SEQUENCE DESCRIPTION: SEQ ID NO:4:

```
Glu Phe Pro Arg Ser Pro Asp Ser Ser Ser Pro Asn Pro Leu Ser Gln
 1               5                  10                  15

Gly Ile Arg Pro Ser Ser Pro Pro Gly Pro Pro Leu Thr Pro Ser Ala
             20                  25                  30

Pro Pro Pro Pro Met Pro Pro Pro Leu Gly Ser Pro Phe Pro Val
             35                  40                  45

Ile Ser Ser Ser Met Gly Ser Pro Gly Leu Pro Pro Pro Ala Pro Pro
         50                  55                  60

Gly Phe Ser Gly Pro Val Ser Ser Pro Gln Ile Asn Ser Thr Val Ser
 65                  70                  75                  80

Leu Pro Gly Gly Gly Ser Gly Pro Pro Glu Asp Val Lys Pro Pro Val
                 85                  90                  95

Leu Gly Val Arg Gly Leu His Cys Pro Pro Pro Gly Gly Pro Gly
            100                 105                 110

Ala Gly Lys Arg Leu Cys Ala Ile Cys Gly Asp Arg Ser Ser Gly Lys
        115                 120                 125

His Tyr Gly Val Tyr Ser Cys Glu Gly Cys Lys Gly Phe Phe Lys Arg
    130                 135                 140

Thr Ile Arg Lys Asp Leu Thr Tyr Ser Cys Arg Asp Asn Lys Asp Cys
145                 150                 155                 160

Thr Val Asp Lys Arg Gln Arg Asn Arg Cys Gln Tyr Cys Arg Tyr Gln
                165                 170                 175

Lys Cys Leu Ala Thr Gly Met Lys Arg Glu Ala Val Gln Glu Glu Arg
            180                 185                 190

Gln Arg Gly Lys Asp Lys Asp Gly Asp Gly Asp Gly Ala Gly Gly Ala
        195                 200                 205

Pro Glu Glu Met Pro Val Asp Arg Ile Leu Glu Ala Glu Leu Ala Val
    210                 215                 220

Glu Gln Lys Ser Asp Gln Gly Val Glu Gly Pro Gly Ala Thr Gly Gly
225                 230                 235                 240

Gly Gly Ser Ser Pro Asn Asp Pro Val Thr Asn Ile Cys Gln Ala Ala
                245                 250                 255

Asp Lys Gln Leu Phe Thr Leu Val Glu Trp Ala Lys Arg Ile Pro His
            260                 265                 270

Phe Ser Ser Leu Pro Leu Asp Asp Gln Val Ile Leu Leu Arg Ala Gly
        275                 280                 285

Trp Asn Glu Leu Leu Ile Ala Ser Phe Ser His Arg Ser Ile Asp Val
    290                 295                 300

Arg Asp Gly Ile Leu Leu Ala Thr Gly Leu His Val His Arg Asn Ser
305                 310                 315                 320

Ala His Ser Ala Gly Val Gly Ala Ile Phe Asp Arg Val Leu Thr Glu
                325                 330                 335
```

| | | | | | | | | | | | | |
|---|---|---|---|---|---|---|---|---|---|---|---|---|
| Leu | Val | Ser | Lys 340 | Met | Arg | Asp | Met 345 | Asp | Lys | Thr 350 | Glu | Leu | Gly |
| Cys | Leu | Arg 355 | Ala | Ile | Ile | Leu | Phe 360 | Asn | Pro | Asp | Ala | Lys 365 | Gly | Leu | Ser |
| Asn | Pro 370 | Gly | Glu | Val | Glu | Ile 375 | Leu | Arg | Glu | Lys | Val 380 | Tyr | Ala | Ser | Leu |
| Glu 385 | Thr | Tyr | Cys | Lys | Gln 390 | Lys | Tyr | Pro | Glu | Gln 395 | Gln | Gly | Arg | Phe | Ala 400 |
| Lys | Leu | Leu | Leu | Arg 405 | Leu | Pro | Ala | Leu | Arg 410 | Ser | Ile | Gly | Leu | Lys 415 | Cys |
| Leu | Glu | His | Leu 420 | Phe | Phe | Phe | Lys | Leu 425 | Ile | Gly | Asp | Thr | Pro 430 | Ile | Asp |
| Thr | Phe | Leu 435 | Met | Glu | Met | Leu | Glu 440 | Ala | Pro | His | Gln | Leu 445 | Ala |